(12) United States Patent
Guo

(10) Patent No.: US 11,583,476 B1
(45) Date of Patent: Feb. 21, 2023

(54) INTELLIGENT PILL BOX

(71) Applicant: ZHUHAI TOP LABEL CO., LTD, Zhuhai (CN)

(72) Inventor: Jinpeng Guo, Zhuhai (CN)

(73) Assignee: ZHUHAI TOP LABEL CO., LTD, Zhuhai (CN)

( * ) Notice: Subject to any disclaimer, the term of this patent is extended or adjusted under 35 U.S.C. 154(b) by 0 days.

(21) Appl. No.: 17/670,541

(22) Filed: Feb. 14, 2022

Related U.S. Application Data

(63) Continuation-in-part of application No. 29/802,081, filed on Aug. 3, 2021, now Pat. No. Des. 943,268.

(51) Int. Cl.
*A61J 7/04* (2006.01)
*A61J 7/00* (2006.01)

(52) U.S. Cl.
CPC ........... *A61J 7/0418* (2015.05); *A61J 7/0069* (2013.01)

(58) Field of Classification Search
CPC .............................. A61J 7/0418; A61J 7/0069
See application file for complete search history.

(56) References Cited

U.S. PATENT DOCUMENTS

| | | | | |
|---|---|---|---|---|
| 11,053,065 B2* | 7/2021 | Brady | ..................... | G16H 20/13 |
| 11,116,698 B2* | 9/2021 | Brady | ..................... | G16H 20/13 |
| 11,224,314 B2* | 1/2022 | Albrecht | ............ | A47K 10/3818 |
| 2006/0091150 A1* | 5/2006 | Ferguson | ............ | H01M 50/271 |
| | | | | 221/270 |
| 2009/0294466 A1* | 12/2009 | Whitson | ............ | G01N 33/4875 |
| | | | | 221/199 |
| 2013/0297068 A1* | 11/2013 | Marshall | ............... | A61J 7/0084 |
| | | | | 700/244 |
| 2014/0339249 A1* | 11/2014 | Reddy | .................... | G16H 20/13 |
| | | | | 221/1 |
| 2018/0039756 A1* | 2/2018 | Phipps | .................... | G16H 40/63 |
| 2021/0100722 A1* | 4/2021 | Hines | ................... | A61B 5/7435 |

* cited by examiner

*Primary Examiner* — Michael Collins

(57) ABSTRACT

The present disclosure provides an intelligent pill box, including a pill box main body, an alarm, and a vibration sensor. The pill box main body is configured to store pills. The alarm is disposed in the pill box main body, and the alarm is configured to remind a user to take the pills. The vibration sensor is disposed on the pill box main body, and the vibration sensor is configured to turn off the alarm when the vibration sensor detects that the pill box main body is rotated. The intelligent pill box may intelligently turn off the alarm, which is convenient for a user to use.

13 Claims, 10 Drawing Sheets

INTELLIGENT PILL BOX

CROSS REFERENCE TO RELATED APPLICATIONS

The present application is a continuation-in-part of a U.S. application Ser. No. 29/802,081, filed on Aug. 3, 2021, and the entire contents of which are hereby incorporated by reference in its entirety

TECHNICAL FIELD

The present disclosure relates to a technical field of electronics, and in particular to an intelligent pill box.

BACKGROUND

Elderly people or people suffering from serious illnesses often need to quantitatively take various pills at regular intervals every day, and they often need help from others in order to correctly take the pills on time. However, even with the help of others, it is still easy to miss or forget to take the pills. In order to help patients regularly and quantitatively take the pills, various intelligent pill boxes appear on market, which are still not intelligent enough.

SUMMARY

The present disclosure provides an intelligent pill box, which improves intelligence of the intelligent pill box.

The intelligent pill box provided by embodiments of the present disclosure includes a pill box main body, an alarm, and a vibration sensor.

The pill box main body is configured to store pills.

The alarm is disposed in the pill box main body, and the alarm is configured to remind a user to take the pills.

The vibration sensor is disposed in the pill box main body, and the vibration sensor is configured to turn off the alarm when the vibration sensor detects that the pill box main body is rotated.

Optionally, the pill box main body includes: a box body, a box cover assembly, a cover body, and a pill tray.

The box cover assembly is connected with the box body, an accommodating space is formed between the box cover assembly and the box body, and a pill taking port is defined on the box cover assembly.

The cover body is disposed in the accommodating space.

The pill tray is disposed in the accommodating space, a mounting hole is defined in a middle of the pill tray, the pill tray is sleeved on the cover body through the mounting hole, the pill tray includes a plurality of pill grids surrounding the cover body, and the pill tray rotates relative to the box cover assembly, so that one of the plurality of the pill grids is correspondingly opposite to the pill taking port.

Optionally, the pill box main body further includes: a driving mechanism and a shifting rod.

The driving mechanism is disposed in the accommodating space.

A first end of the shifting rod is connected with the driving mechanism, and a second end of the shifting rod is in driving connection with the pill tray.

The driving mechanism drives the shifting rod to rotate, so that the shifting rod drives the pill tray to rotate.

Optionally, a plurality of shifting grooves are defined in one side, distal from the box cover assembly, of the pill tray.

Shifting pieces are disposed on the second end of the shifting rod, and the shifting pieces are clamped into the shifting grooves to drive the pill tray to rotate.

Optionally, the driving mechanism includes: a motor, a reduction gear set, and an output gear.

The motor is disposed on the box body.

The reduction gear set is connected to an output end of the motor.

The output gear is rotatably connected with the reduction gear set, and the output gear is further detachably connected with the shifting rod.

Optionally, the shifting rod includes an annular skirt having a plurality of notches.

The intelligent pill box further includes an infrared sensing device, the infrared sensing device includes an infrared emitter and an infrared receiver, and the infrared emitter and the infrared receiver are disposed on the two sides of the annular skirt.

When the annular skirt is rotated between the infrared emitter and the infrared receiver, the infrared receiver cannot receive infrared light emitted by the infrared emitter, and the infrared receiver controls the alarm to emit reminding information.

When the notches are located between the infrared emitter and the infrared receiver, the infrared receiver receives the infrared light emitted by the infrared emitter, and the infrared receiver controls the driving mechanism to stop working.

Optionally, the intelligent pill box further includes a timer.

The timer is disposed on the pill box main body, and the timer is configured to control the driving mechanism to start working when preset time of the timer is arrived, so that the annular skirt is rotated between the infrared emitter and the infrared receiver.

Optionally, the box cover assembly includes a box cover and a sliding cover. The sliding cover is slidably disposed on the box cover, and the sliding cover slides relative to the box cover so as to block the pill taking port or expose the pill taking port.

Optionally, the box cover assembly further includes an observation port. The observation port is adjacent to the pill taking port where the pill taking port is correspondingly opposite to the one of the plurality of the pill grids, each of the pill grids of the pill tray is provided with a corresponding number of times of taking pills and the observation port is configured to show the corresponding number of the times of taking the pills of each of the pill grids.

Optionally, the intelligent pill box further includes: a display and a time setting function key.

The display is disposed on the pill box main body, and the display is configured to display a system time and set a pill taking reminding time.

The time setting function key is disposed on the pill box main body, and the time setting function key is configured to adjust the system time and preset the pill taking reminding time.

Optionally, the display is disposed on the box body, a first through hole, corresponding to the display, is defined on the cover body. A material of the box cover assembly is a transparent material.

Optionally, the box body further includes a lock pin groove. A lock hole, corresponding to the lock pin groove, is defined on the box cover assembly.

The intelligent pill box further includes a lock pin, and the lock pin penetrates through the lock pin groove to lock with the lock hole, so as to tightly lock the box body and the box cover assembly.

Optionally, the lock pin rotates relative to the lock hole to lock or unlock the lock pin with the lock hole.

Optionally, the intelligent pill box further includes a key, the key is detachably connected with the lock pin, and the key drives the lock pin to rotate.

Optionally, a key groove is defined in one side, distal from the box cover assembly, of the box body. The key is detachably disposed in the key groove.

Optionally, the alarm includes a prompting lamp, and the prompting lamp is disposed on one side, facing the box cover assembly, of the cover body.

Optionally, the alarm includes a loudspeaker, and the loudspeaker is disposed in the pill box main body.

Optionally, the intelligent pill box further includes a microprocessor and a wireless communication unit. Both the vibration sensor and the wireless communication unit are connected with the microprocessor. The microprocessor acquires rotation information, detected by the vibration sensor, of the pill box main body, and the microprocessor sends the rotation information to external equipment through the wireless communication unit.

In embodiments of the present disclosure, the pill box main body is configured to store the pills, the alarm reminds the user to take the pills stored in the pill box main body, and the alarm may send out remindings through audio, light, etc. When the user needs to take the pills stored in the pill box main body, the pill box main body is rotated to pour out the pills from the pill box main body. At this time, the vibration sensor detects rotation of the pill box main body, and the vibration sensor may deduce that the user already knows that the pills need to be taken out from the pill box main body, so that the vibration sensor may intelligently turn off the alarm. Compared with a pill box requiring the user to manually close the alarm in related art, the intelligent pill box provided by the embodiments of the present disclosure is more intelligent. Moreover, users using the intelligent pill box are generally elderly people or people suffering from serious illnesses, and hands of the users are often not flexible. Some users even cannot accurately trigger an off switch, and manually turning off the alarm may take a longer time. Further, the alarm generally adopts a relatively sharp reminding tone, so that the users hear the uncomfortable reminding tone for a long time, which causes great discomfort to ears and mood of the users. According to the intelligent pill box provided by the embodiments of the present disclosure, when the intelligent pill box detects that the intelligent pill box rotates, the alarm is turned off, the users do not need to find the off switch again, the alarm may be turned off more quickly, which is convenient for the user to use, and power consumption of the intelligent pill box may be reduced.

BRIEF DESCRIPTION OF DRAWINGS

In order to more clearly illustrate technical solutions in embodiments of the present disclosure, drawings required in description of the embodiments are briefly described below. Obviously, the drawings in the following description are merely some embodiments of the present disclosure, and for a person skilled in art, other drawings may be obtained according to the drawings without creative efforts.

For a more complete understanding of the present disclosure and beneficial effects of the present disclosure, the following description is made with reference to the accompanying drawings, in which same reference numerals refer to same parts in the following description.

DETAILED DESCRIPTION

Technical solutions in embodiments of the present disclosure are clearly and completely described below with reference to accompanying drawings in the embodiments of the present disclosure. Obviously, the described embodiments are only a part of the embodiments of the present disclosure, rather than all of the embodiments. Based on the embodiments in the present disclosure, all other embodiments obtained by a person skilled in art without creative efforts shall fall within a protection scope of the present disclosure.

Figure 1:
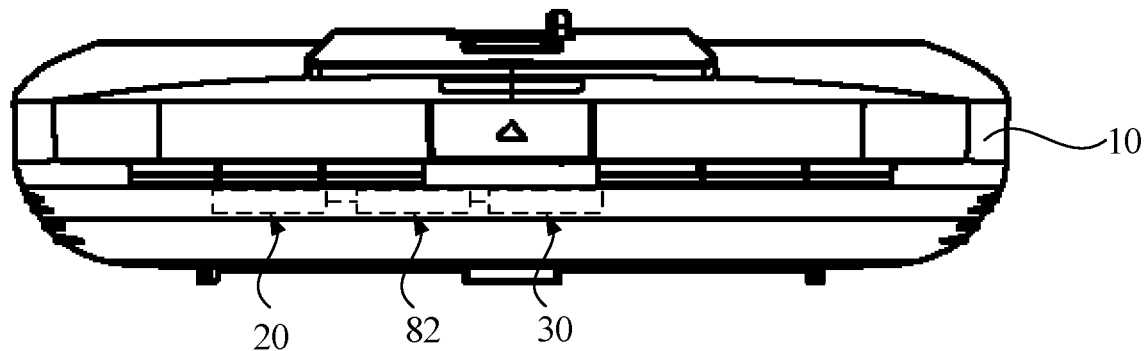
FIG. 1 is a first structural schematic diagram of an intelligent pill box according to one embodiment of the present disclosure.

The embodiments of the present disclosure provide an intelligent pill box. Please refer to FIG. 1, where FIG. 1 is a first structural schematic diagram of an intelligent pill box according to one embodiment of the present disclosure. The intelligent pill box 1 includes a pill box main body 10, an alarm 20, and a vibration sensor 30. The pill box main body 10 is configured to store pills. The alarm 20 is disposed in the pill box main body 10, and the alarm 20 is configured to remind a user to take the pills. For example, the alarm 20 reminds the user to take the pills stored in the pill box main body 10, and the alarm 20 may send out remindings through audio, light, etc. The vibration sensor 30 is disposed in the pill box main body 10, and the vibration sensor 30 is configured to turn off the alarm 20 when the vibration sensor 30 detects that the pill box main body 10 is rotated. For example, when the user needs to take the pills stored in the pill box main body 10, the pill box main body 10 is rotated to pour out the pills from the pill box main body 10. At this time, the vibration sensor 30 detects rotation of the pill box main body 10, and the vibration sensor 30 may deduce that the user already knows that the pills need to be taken out from the pill box main body 10, so that the vibration sensor 30 may intelligently turn off the alarm 20. The user does not need to manually turn off a reminder function, which operation is simple. Compared with a pill box that requires the user to manually turn off the alarm in related art, the intelligent pill box 1 provided by the embodiments of the present disclosure is more intelligent. Moreover, users using the intelligent pill box are generally elderly people or people suffering from serious illnesses, and hands of the users are often not flexible. Some users even cannot accurately trigger an off switch, manually turning off the alarm may take a longer time. Further, the alarm 20 generally adopts a relatively sharp reminding tone, so that the users hear the uncomfortable reminding tone for a long time, which causes great discomfort to ears and mood of the users. According to the intelligent pill box 1 provided by the embodiments of the present disclosure, when the intelligent pill box 1 detects that the intelligent pill box 1 rotates, the alarm 20 is turned off, the user does not need to find the off switch again, the alarm 20 may be turned off more quickly, which is convenient for the user to use, and power consumption of the intelligent pill box may be reduced.

It should be noted that the vibration sensor 30 may detect a range of a rotation angle of the pill box main body 10. For example, when the rotation angle of the pill box main body 10 exceeds 30 degrees or 60 degrees, the vibration sensor 30 may recognize and turn off the alarm 20. For another example, the vibration sensor 30 is turned off when the pill box main body 10 is laid flat, the vibration sensor 30 is turned on when the pill box main body 10 is erected. When the vibration sensor 30 is turned on, the alarm 20 stops working.

Figure 2:
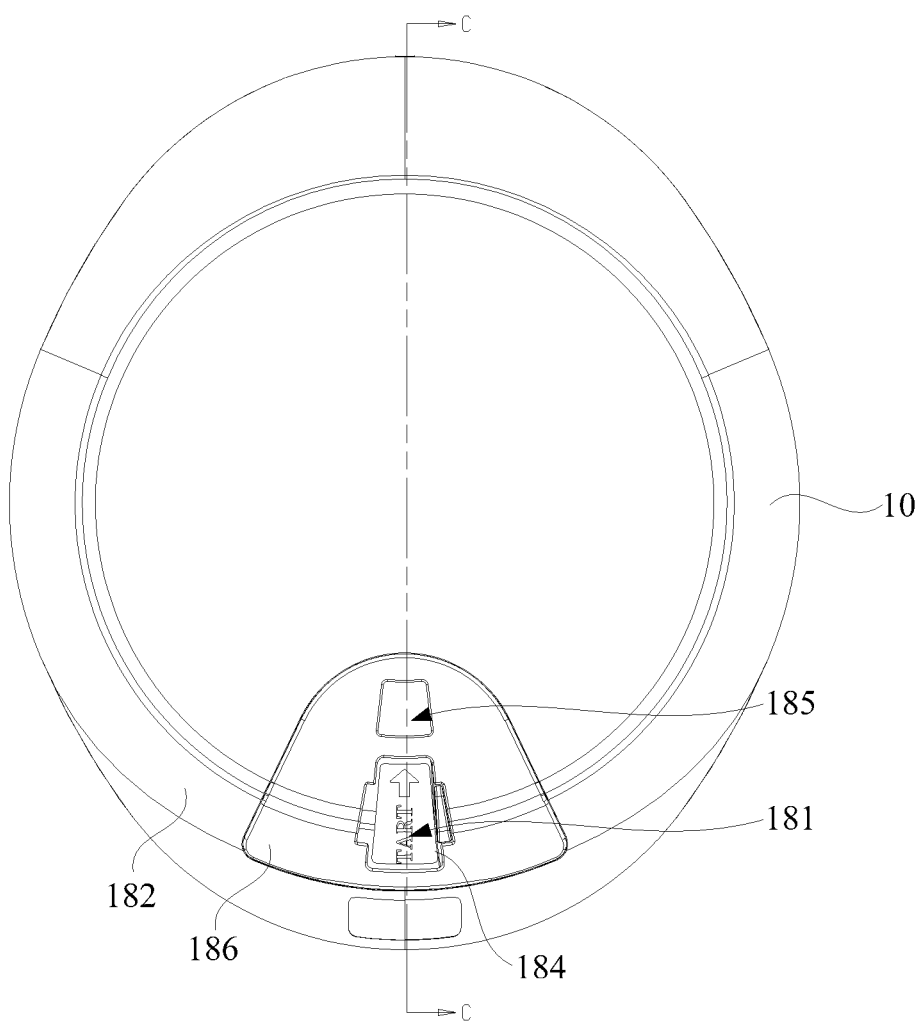
FIG. 2 is a second structural schematic diagram of an intelligent pill box according to one embodiment of the present disclosure.
Figure 3:
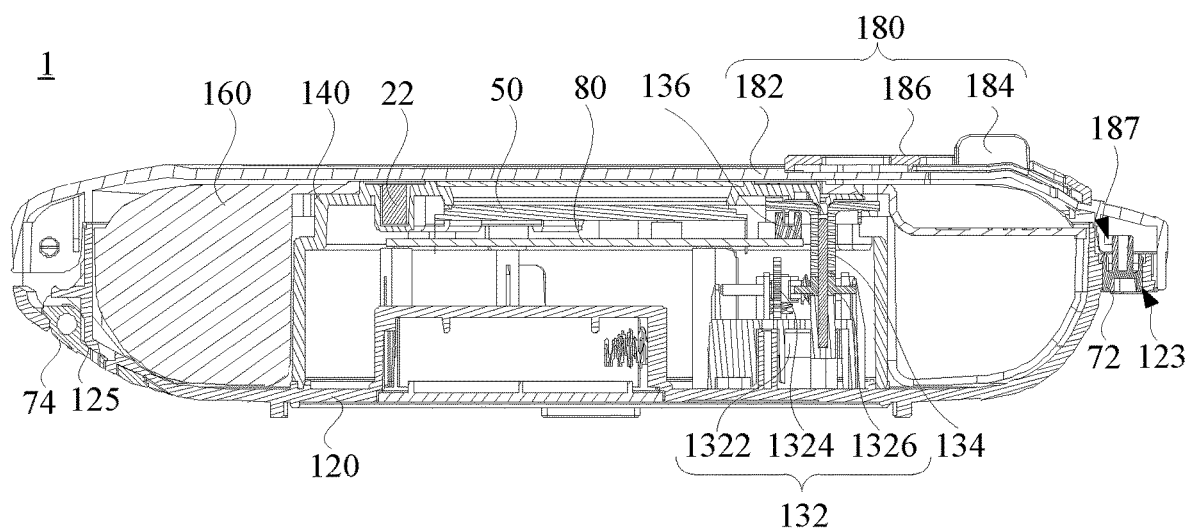
FIG. 3 is a cross-sectional schematic diagram taken along line C-C of FIG. 2 of the intelligent pill box.
Figure 4:
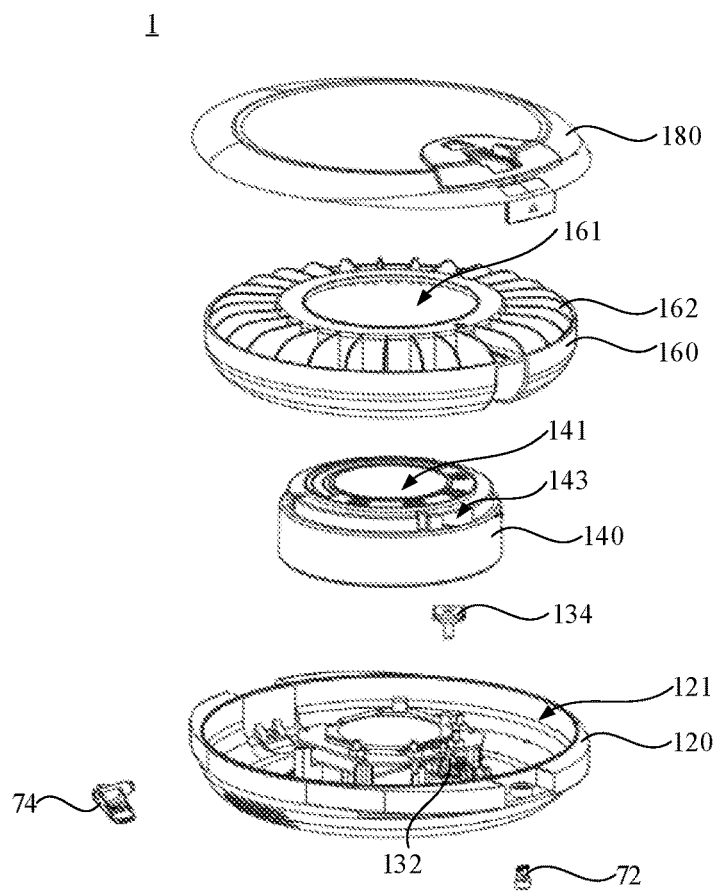
FIG. 4 is an exploded schematic diagram of the intelligent pill box shown in FIG. 2.

Please refer to FIG. 2, FIG. 3, and FIG. 4, where FIG. 2 is a second structural schematic diagram of an intelligent pill box according to one embodiment of the present disclosure, FIG. 3 is a cross-sectional schematic diagram taken along line C-C of FIG. 2 of the intelligent pill box, and FIG. 4 is an exploded schematic diagram of the intelligent pill box shown in FIG. 2. The pill box main body 10 includes a box body 120, a cover body 140, a pill tray 160, and a box cover assembly 180. The box cover assembly 180 is connected with the box body 120, an accommodating space 121 is formed between the box cover assembly 180 and the box body 120, and a pill taking port 181 is defined on the box cover assembly 180. The box body 120 and the box cover assembly 180 constitute a main frame of the intelligent pill box 1. The cover body 140 is disposed in the accommodating space 121. The pill tray 160 is disposed in the accommodating space 121, a mounting hole 161 is defined in a middle of the pill tray 160, the pill tray 160 is sleeved on the cover body 140 through the mounting hole 161, the pill tray 160 includes a plurality of pill grids 162 surrounding the cover body 140, and the pill tray 160 rotates relative to the box cover assembly 180, so that one of the plurality of the pill grids 162 is correspondingly opposite to the pill taking port 181. The plurality of the pill grids 162 of the pill tray 160 are independently disposed, and each of the plurality of pill grids 162 may store the pills that the user takes at one time. The pill tray 160 rotates relative to the box cover assembly 180, so that different pill grids 162 may be correspondingly rotated to the pill taking port 181, and the pills in the corresponding pill grids 162 are taken out through the pill taking port 181. For example, the pill box main body 10 is inverted, so that the pills in the pill grids 162 are poured out through the pill taking port 181.

The pill box main body 10 further includes a driving mechanism 132 and a shifting rod 134. The driving mechanism 132 is disposed in the accommodating space 121. A first end of the shifting rod 134 is connected with the driving mechanism 132, and a second end of the shifting rod 134 is in driving connection with the pill tray 160. The driving mechanism 132 drives the shifting rod 134 to rotate, so that the shifting rod 134 drives the pill tray 160 to rotate. The driving mechanism 132 drives the pill tray 160 to rotate through the shifting rod 134, so that the different pill grids 162 may be correspondingly rotated to the pill taking port 181.

Figure 5:
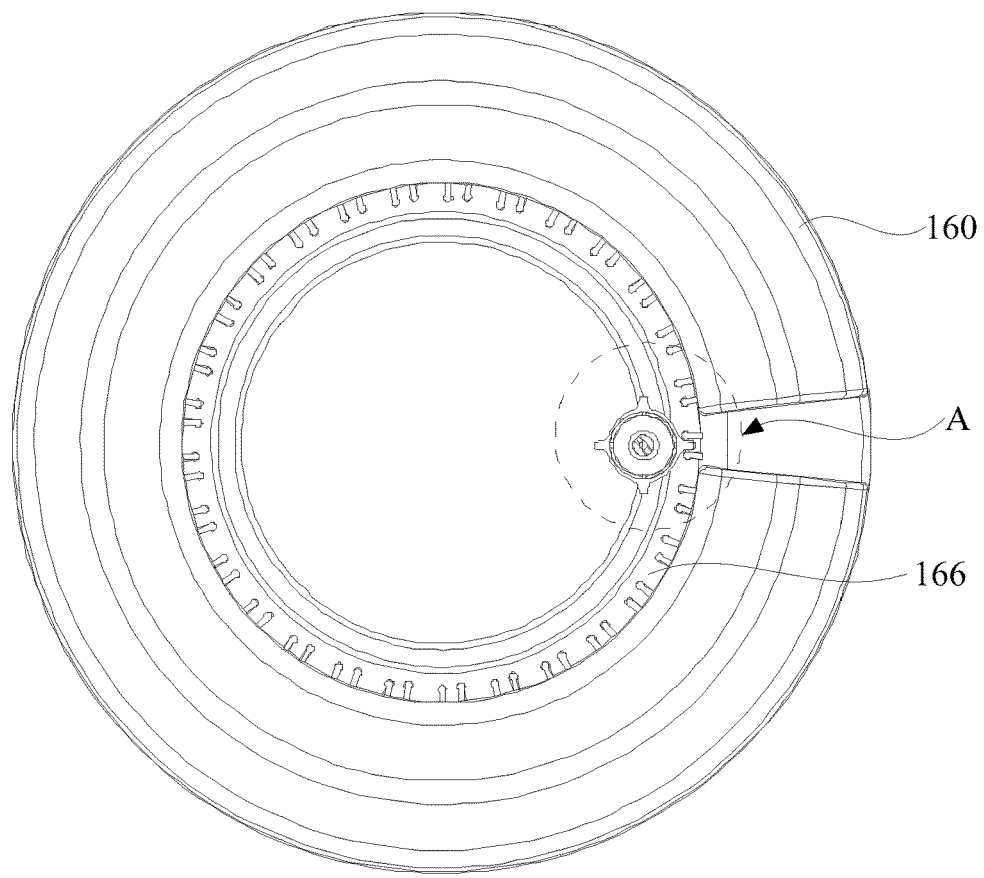
FIG. 5 is a structural schematic diagram of a pill tray and a shifting rod of the intelligent pill box shown in FIG. 2.
Figure 6:
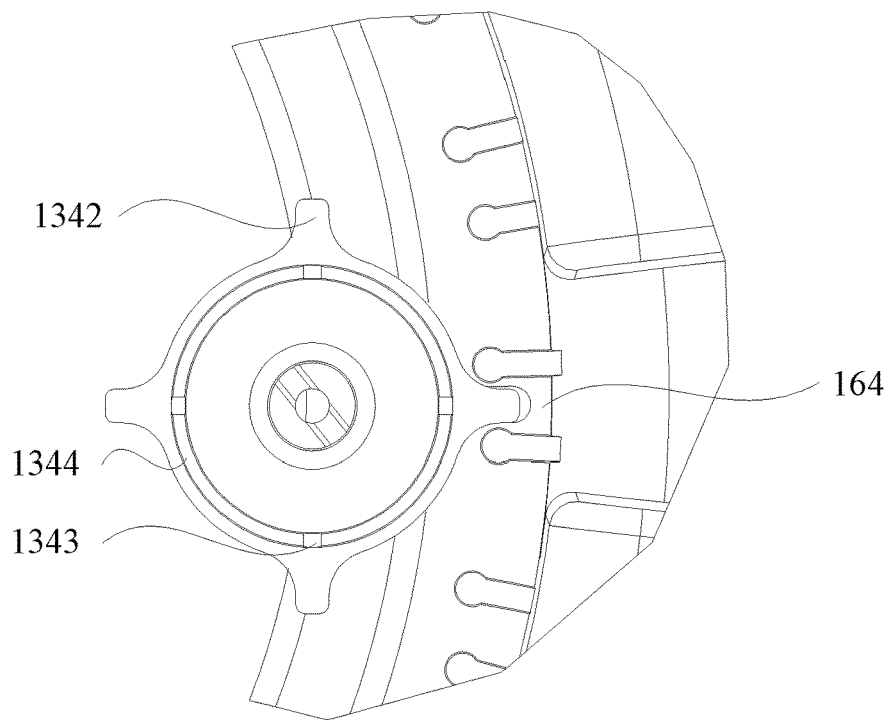
FIG. 6 is an enlarged schematic diagram of portion A of the pill tray and the shifting rod shown in FIG. 5.
Figure 7:
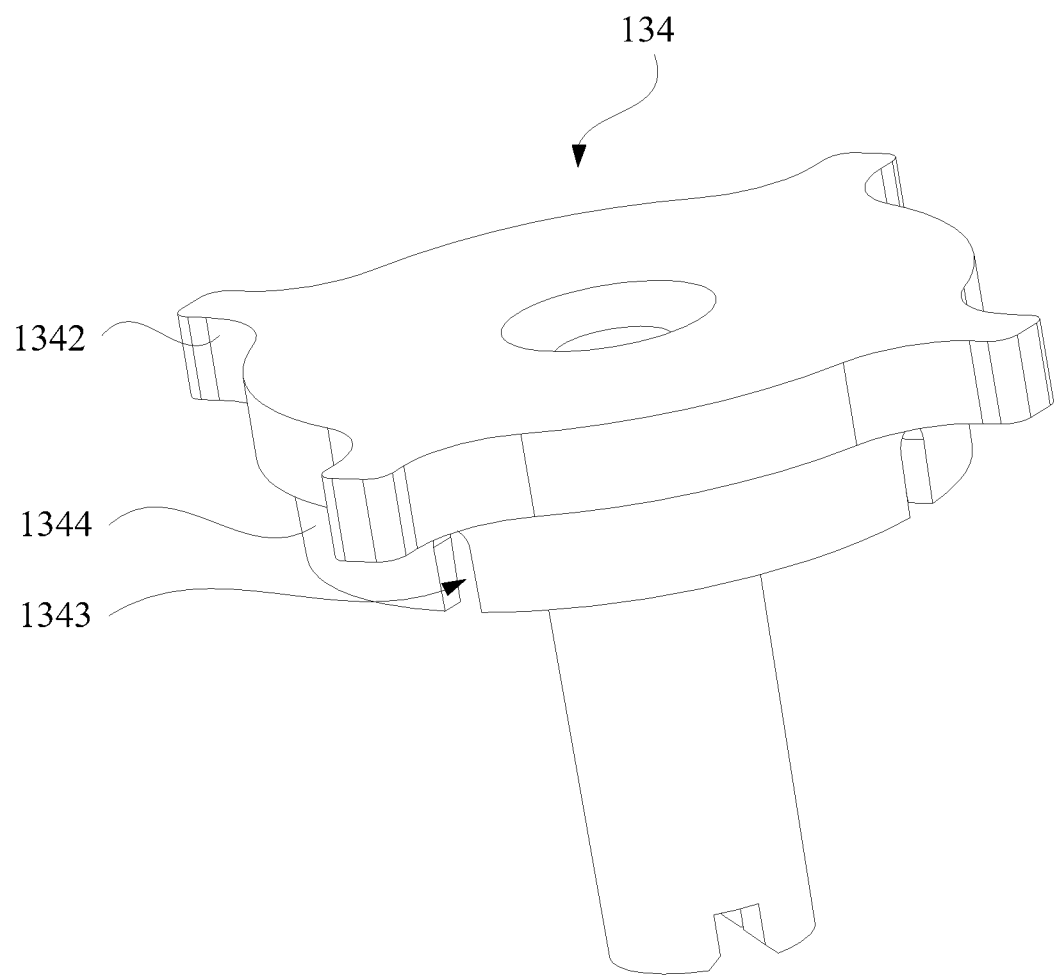
FIG. 7 is a structural schematic diagram of the shifting rod of the intelligent pill box shown in FIG. 2.

Please refer to FIG. 4, and in conjunction with FIG. 5, FIG. 6 and FIG. 7, where FIG. 5 is a structural schematic diagram of a pill tray and a shifting rod of the intelligent pill box shown in FIG. 2, FIG. 6 is an enlarged schematic diagram of portion A of the pill tray and the shifting rod shown in FIG. 5, and FIG. 7 is a structural schematic diagram of the shifting rod of the intelligent pill box shown in FIG. 2. A cover body notch 143 is defined on the cover body 140, and the shifting rod 134 may extend out from the cover body notch 143 to be matched with the pill tray 160 to rotate. Specifically, a plurality of shifting grooves 164 are defined in one side, distal from the box cover assembly 180, of the pill tray 160. The second end of the shifting rod 134 may extend out of the cover body notch 143 of the cover body 140, shifting pieces 1342 are disposed on the second end of the shifting rod 134, and the shifting pieces 1342 are clamped into the shifting grooves 164 to drive the pill tray 160 to rotate. For example, a plurality of shifting pieces 1342 are disposed on the second end of the shifting rod 134 at intervals, and when the shifting rod 134 rotates, one of the shifting pieces 1342 may move out of the shifting grooves 164 into the shifting grooves 164, so that the shifting grooves 164 are pushed to rotate, and the pill tray 160 is driven to rotate. After the shifting rod 134 rotates by a certain angle, the corresponding shifting piece 1342 is moved out from the shifting grooves 164 and is separated from the shifting grooves 164. Another shifting piece 1342 may be moved out of the shifting grooves 164 into the shifting grooves 164, so as to continue to push the pill tray 160 to rotate.

The shifting rod 134 includes an annular skirt 1344 having a plurality of notches 1343. The intelligent pill box 1 further includes an infrared sensing device 136, the infrared sensing device 136 includes an infrared emitter 1362 and an infrared receiver 1364, and the infrared emitter 1362 and the infrared receiver 1364 are disposed on the two sides of the annular skirt 1344. When the annular skirt 1344 is rotated between the infrared emitter 1362 and the infrared receiver 1364, the infrared receiver 1364 cannot receive infrared light emitted by the infrared emitter 1362, and the infrared receiver 1364 controls the alarm 20 to emit reminding information. When the notches 1343 are located between the infrared emitter 1362 and the infrared receiver 1364, the infrared receiver 1364 receives the infrared light emitted by the infrared emitter 1362, and the infrared receiver 1364 controls the driving mechanism 132 to stop working.

Please refer to FIG. 3, the driving mechanism 132 includes a motor 1322, a reduction gear set 1324, and an output gear 1326. The motor 1322 is disposed on the box body 120. The reduction gear set 1324 is connected to an output end of the motor 1322. The output gear 1326 is rotatably connected with the reduction gear set 1324, and the output gear 1326 is further detachably connected with the shifting rod 134. The reduction gear set 1324 controls a rotating speed of the output gear 1326, so that a rotating speed of the shifting rod 134 and the pill tray 160 is conveniently controlled. For example, the pill tray 160 is controlled to only rotate one of the pill grids 162, namely that, the next one of the pill grids 162 is rotated to the corresponding pill taking port 181.

Figure 8:
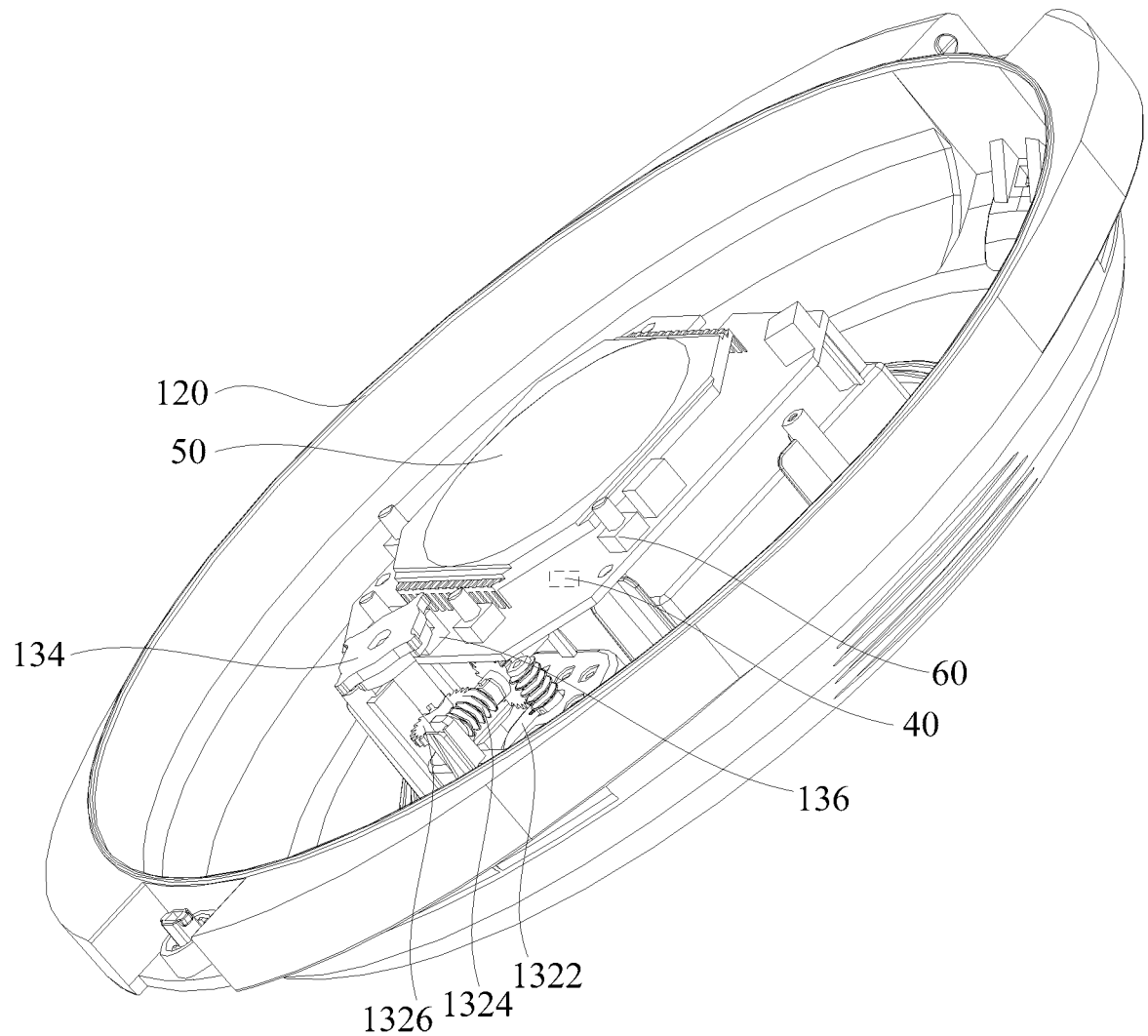
FIG. 8 is a structural schematic diagram of a first portion of the intelligent pill box shown in FIG. 2.

Please refer to FIG. 8, where FIG. 8 is a structural schematic diagram of a first portion of the intelligent pill box shown in FIG. 2. The intelligent pill box 1 further includes a timer 40. The timer 40 is disposed on the pill box main body 10, and the timer 40 is configured to control the driving mechanism 132 to start working when preset time of the timer 40 is arrived, so that the annular skirt 1344 is rotated between the infrared emitter 1362 and the infrared receiver 1364.

Please continue to refer to FIG. 8, the intelligent pill box 1 further includes a display 50 and a time setting function key 60. The display 50 is disposed on the pill box main body 10, and the display 50 is configured to display a system time and set a pill taking reminding time. The time setting function key 60 is disposed on the pill box main body 10, and the time setting function key 60 is configured to adjust the system time and preset the pill taking reminding time.

The display 50 is disposed on the box body 120, a first through hole 141, corresponding to the display 50, is defined on the cover body 140. A material of the box cover assembly 180 is a transparent material. The user may see the display 50 through the box cover assembly 180 of the transparent material and the first through hole 141. The material of the box cover assembly 180 may be set as required, for example, the material of the box cover assembly 180 may be one of transparent glass, transparent plastic, transparent resin, etc.

Figure 9:
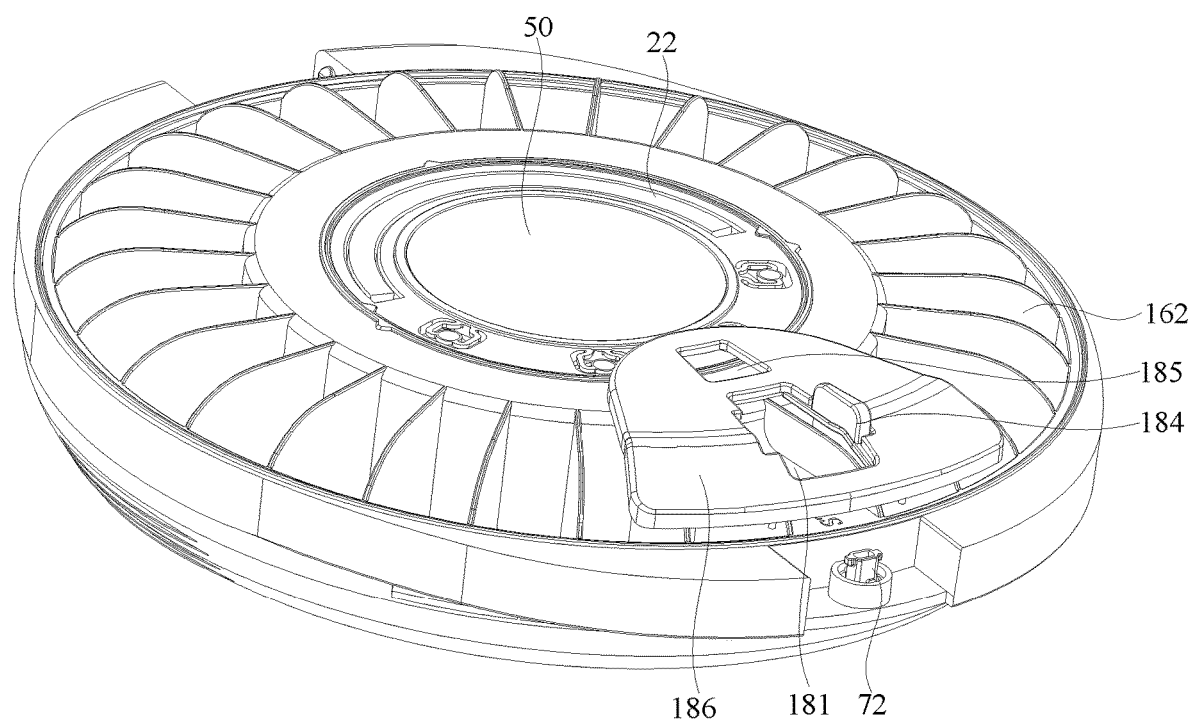
FIG. 9 is a structural schematic diagram of a second portion of the intelligent pill box shown in FIG. 2.

Please refer to FIG. 9, where FIG. 9 is a structural schematic diagram of a second portion of the intelligent pill box shown in FIG. 2. The box cover assembly 180 includes a box cover 182 and a sliding cover 184. The sliding cover 184 is slidably disposed on the box cover 182, and the sliding cover 184 slides relative to the box cover 182 so as to block the pill taking port 181 or expose the pill taking port 181. For example, a main body of the sliding cover 184 may be disposed inside the box cover 182, and the sliding cover 184 may further includes a handle protruding from the pill taking port 181. The user may push the sliding cover 184 to slide through the handle, so as to expose the pill taking port 181 or block the pill taking port 181.

It should be understood that a positioning structure clamped with the sliding cover 184 may be disposed on the box cover 182, and the sliding cover 184 may be positioned, so that the sliding cover 184 may stably block the pill taking port 181. The positioning structure may be a clamping structure. In some other embodiments, magnetic attraction positioning structures matched with each other may disposed on the box cover 182 and the sliding cover 184, so that the sliding cover 184 and the box cover 182 are magnetically attracted together. For example, a magnet is disposed on the box cover 182, and a metal or another magnet matched with the magnet is disposed on the sliding cover 184. For another example, a magnet is disposed on the sliding cover 184, and a metal or another magnet matched with the magnet is disposed on the box cover 182.

The box cover assembly 180 further includes an observation port 185. The observation port 185 is adjacent to the pill taking port 181, where the pill taking port 181 is correspondingly opposite to the one of the plurality of the pill grids 162, each of the pill grids 162 of the pill tray 160 is provided with a corresponding number of times of taking pills and the observation port 185 is configured to show the corresponding number of the times of taking the pills of each of the pill grids 162. For example, the box cover assembly 180 may include the box cover 182, the sliding cover 184, and a cover plate 186. Structures of the box cover 182 and the sliding cover 184 may be obtained through the above embodiments, and details are not described herein again. The cover plate 186 is detachably connected to the box cover 182. The observation port 185 may be disposed on the cover plate 186 or on the box cover 182. For another example, the observation port 185 may correspond to an annular convex edge 166 of the pill tray 160, and a position of the corresponding pill grid 162 on the annular convex edge 166 may be pasted or engraved with a typeface of the number of the times of taking the pills (such as 1, 2, 3, etc.), and the user may view the current number of the times of taking the pills through the observation port 185. Certainly, in some other embodiments, the number of the times of taking the pills may be further set at other positions of the pill tray 160. The observation port 185 may be a through hole or may be made of the transparent material.

Figure 10:
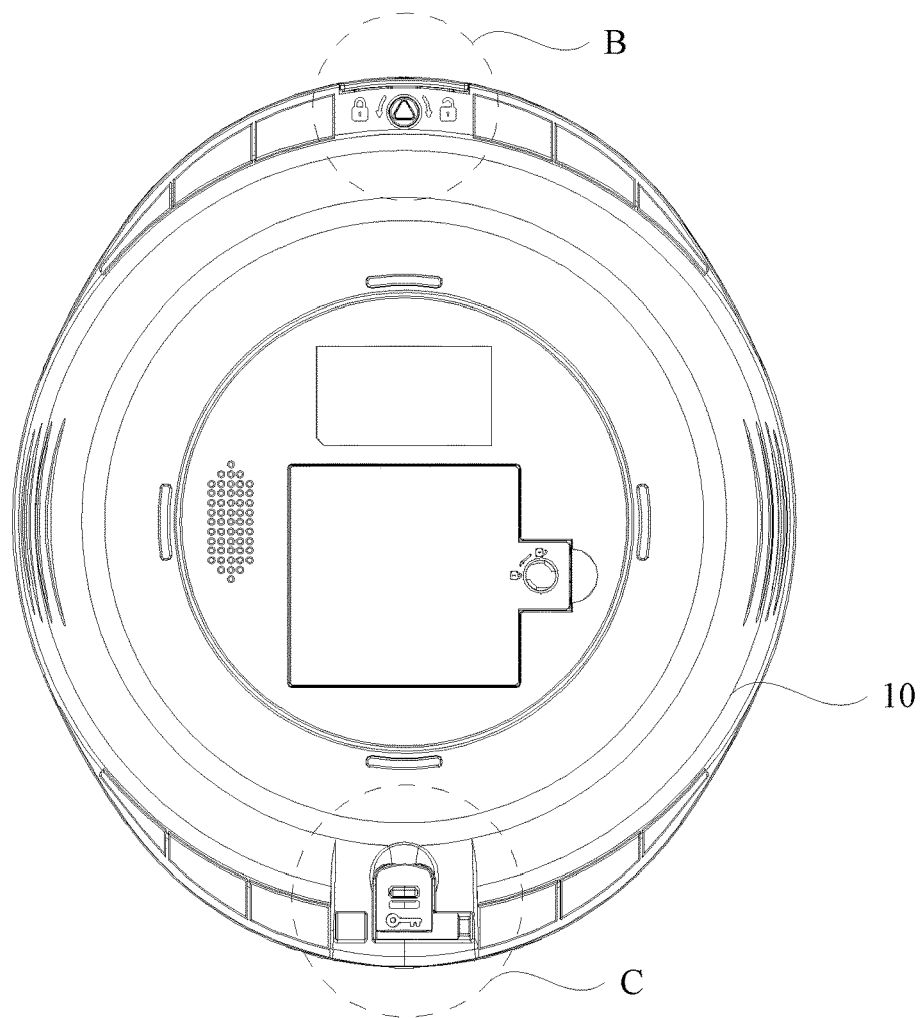
FIG. 10 is a structural schematic diagram of another angle of the intelligent pill box shown in FIG. 2.
Figure 11:
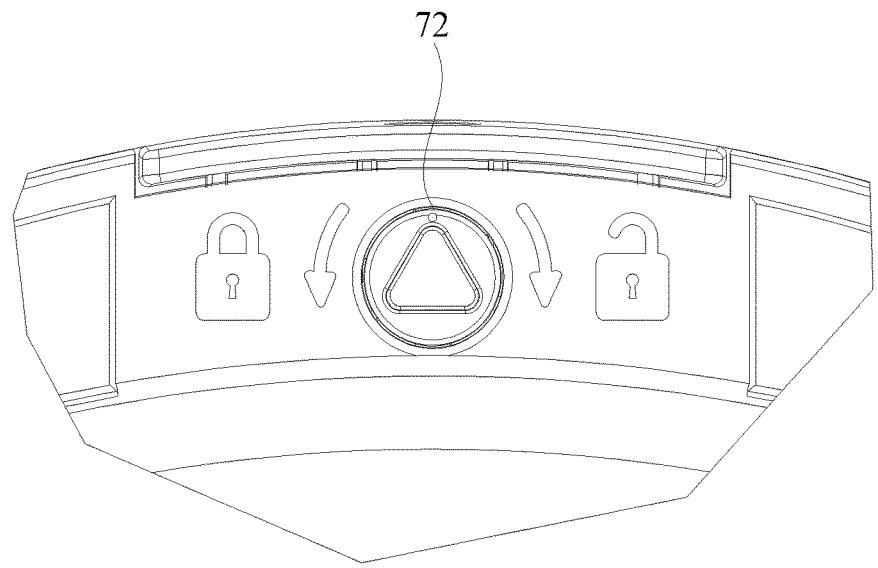
FIG. 11 is an enlarged schematic diagram of portion B of the intelligent pill box shown in FIG. 10.
Figure 12:
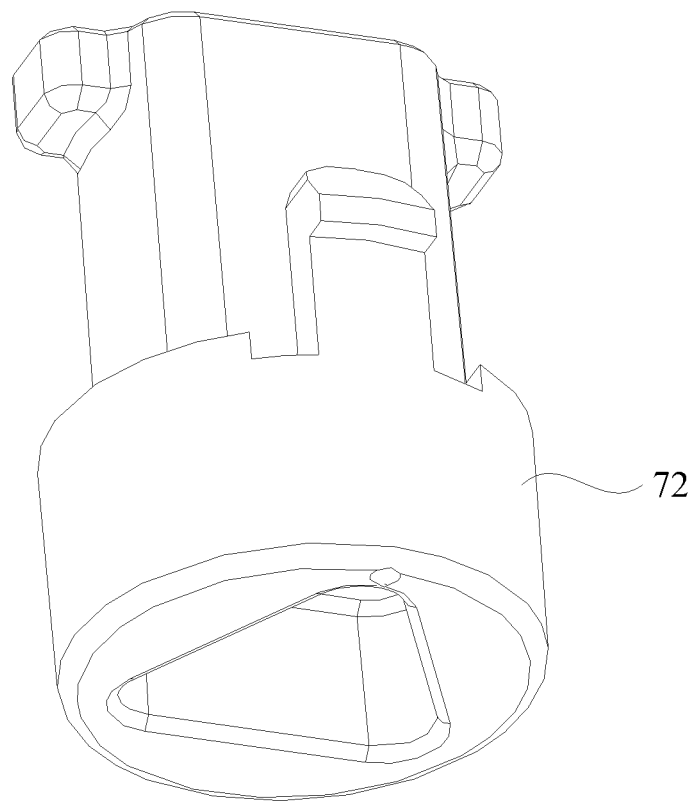
FIG. 12 is a structural schematic diagram of a lock pin in the intelligent pill box shown in FIG. 10.

Please refer to FIG. 10, FIG. 11, and FIG. 12, where FIG. 10 is a structural schematic diagram of another angle of the intelligent pill box shown in FIG. 2, FIG. 11 is an enlarged schematic diagram of portion B of the intelligent pill box shown in FIG. 10, and FIG. 12 is a structural schematic diagram of a lock pin in the intelligent pill box shown in FIG. 10. The box body 120 further includes a lock pin groove 123. A lock hole 187, corresponding to the lock pin groove 123, is defined on the box cover assembly 180. The intelligent pill box 1 further includes a lock pin 72, and the lock pin 72 penetrates through the lock pin groove 123 to lock with the lock hole 187, so as to tightly lock the box body 120 and the box cover assembly 180. Only after the user takes out the lock pin 72 from the lock hole 187, the box cover assembly 180 may be opened, so as to place the pills in the pill grids 162 of the pill tray 160. Before the lock pin 72 is removed from the lock hole 187, the box cover assembly 180 cannot be opened, so as to avoid the box cover assembly 180 from being opened by mistake and protect safety of the pills in the pill tray 160. It should be noted that after the lock pin 72 is removed from the lock hole 187, the lock pin groove 123 may still limit the lock pin 72, so as to prevent the lock pin 72 from being lost. Certainly, in some other embodiments, the lock pin 72 may further be removed from the lock pin groove 123.

The lock pin 72 rotates relative to the lock hole 187 to lock or unlock the lock pin 72 with the lock hole 187. For example, a protrusion is defined on an end portion of the lock pin 72, and the end portion of the lock pin 72 may be clamped into the lock hole 187 along a preset angle. The lock pin 72 may rotate in the lock hole 187, the protrusion of the end portion of the lock pin 72 is clamped to a limiting structure of an inner wall of the lock hole 187 after rotating, so that the lock pin 72 cannot be separated from the lock hole 187, thereby the lock pin 72 is locked with the lock hole 187. When the lock pin 72 needs to be taken out, the lock pin 72 is rotated, so that the protrusion of the end portion of the lock pin 72 is separated from the limiting structure of the inner wall of the lock hole 187. Then, the lock pin 72 may be removed from the lock hole 187, so as to unlock the lock pin 72 and the lock hole 187.

Figure 13:
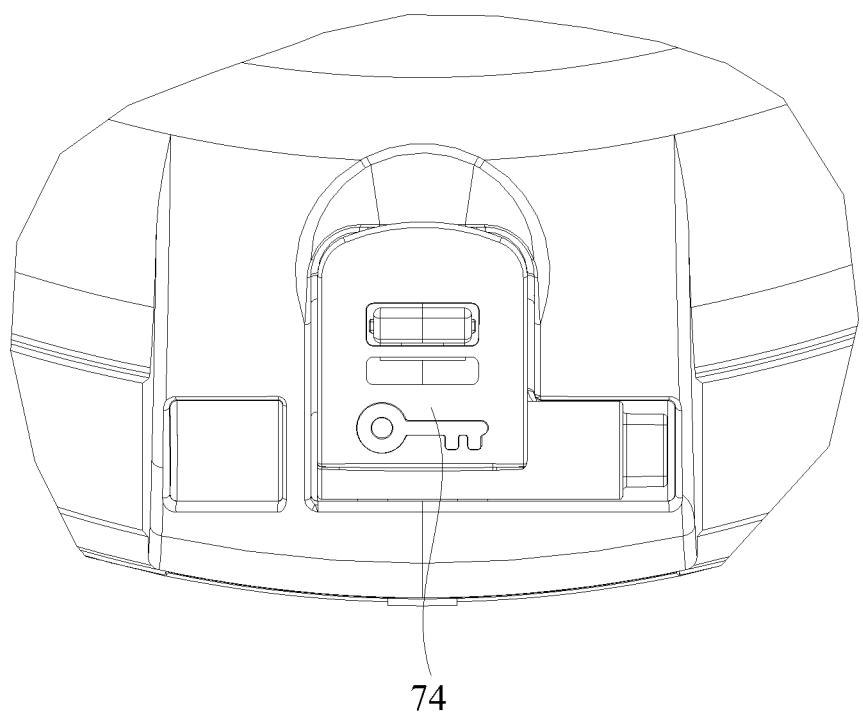
FIG. 13 is an enlarged schematic diagram of portion C of the intelligent pill box shown in FIG. 10.
Figure 14:
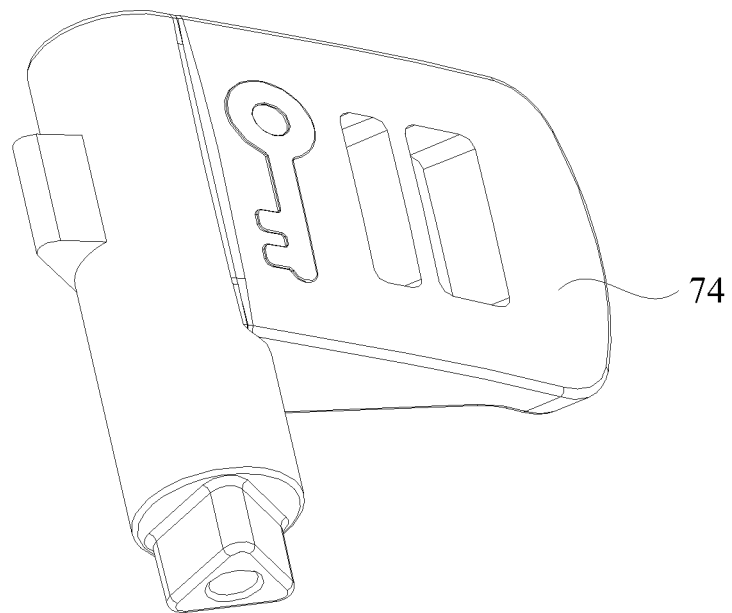
FIG. 14 is a structural schematic diagram of a key of the intelligent pill box shown in FIG. 10.

Please refer to FIG. 13 and FIG. 14, where FIG. 13 is an enlarged schematic diagram of portion C of the intelligent pill box shown in FIG. 10 and FIG. 14 is a structural schematic diagram of a key of the intelligent pill box shown in FIG. 10. The intelligent pill box 1 further includes a key 74, the key 74 is detachably connected with the lock pin 72, and the key 74 drives the lock pin 72 to rotate. For example, a triangular groove is defined on the end portion of the lock pin 72, a triangular protrusion portion matched the triangular groove is defined on an end portion of the key 74, and the triangular protrusion portion of the key 74 may be clamped into the triangular groove. A tail portion of the key 74 may be configured as a holding portion, the user holds the holding portion to rotate to drive the lock pin 72 to rotate, thereby realizing locking and unlocking of the lock pin 72 and the locking hole 187.

It should be noted that the lock pin 72 is almost completely clamped in the pill box main body 10. If there is no key 74, the lock pin 72 is not easy to rotate, so that the intelligent pill box 1 is not easy to be opened, and the safety of the pills in the intelligent pill box 1 is ensured.

A key groove 125 is defined in one side, distal from the box cover assembly 180, of the box body 120. The key 74 is detachably disposed in the key groove 125, so that the key 74 may be conveniently stored, the key 74 may follow the pill box main body 10, and the key 74 is not easy to lose.

Please continue to refer to FIG. 9. The alarm 20 includes a prompting lamp 22, and the prompting lamp 22 is disposed on one side, facing the box cover assembly 180, of the cover body 140. The prompting lamp 22 may second out remindings through normal brightness, flicker, etc. The prompting lamp 22 may be an LED lamp or other kinds of lamps. A color of the prompting lamp 22 may be set as required, such as one or more of red, blue, green, orange, white, etc.

Figure 15:
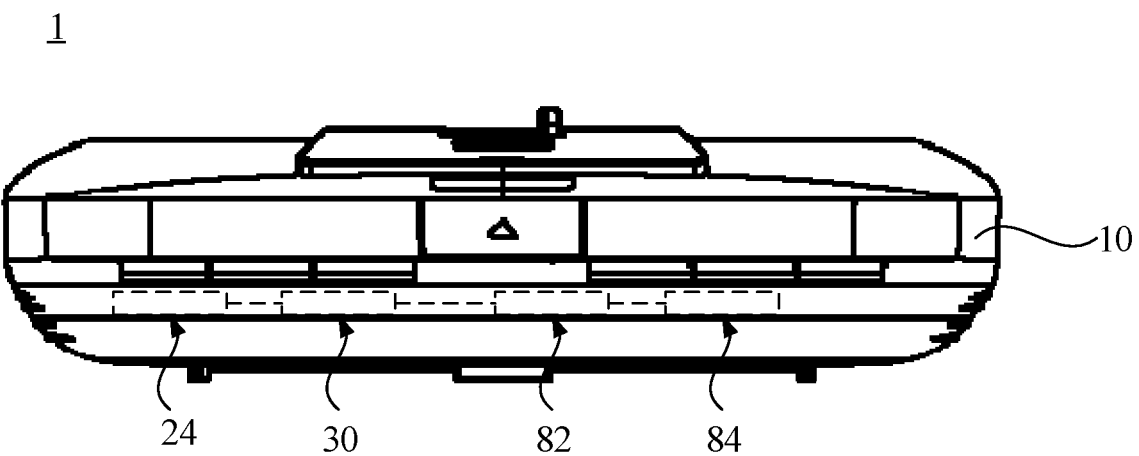
FIG. 15 is a third structural schematic diagram of an intelligent pill box according to one embodiment of the present disclosure.

Please refer to FIG. 15, where FIG. 15 is a third structural schematic diagram of an intelligent pill box according to one embodiment of the present disclosure. The alarm 20 includes a loudspeaker 24, and the loudspeaker 24 is disposed in the pill box main body 10. The loudspeaker 24 may send out remindings through audio, and a volume of the loudspeaker 24 may gradually increase according to a duration of reminding. The loudspeaker 24 may be a speaker or a buzzer, etc.

The intelligent pill box 1 further includes a microprocessor 82 and a wireless communication unit 84. Both the vibration sensor 30 and the wireless communication unit 84 are connected with the microprocessor 82. The microprocessor 82 acquires rotation information, detected by the vibration sensor 30, of the pill box main body 10, and the microprocessor 82 sends the rotation information to external equipment through the wireless communication unit 84. It may be understood that according to the alarm 20 and the vibration sensor 30, the microprocessor 82 may know pill taking information such as whether pill taking time has been reached, and whether the user has taken pills or not, etc. The microprocessor 82 may send the pill taking information to an external device such as a mobile phone through the wireless communication unit 84, so that the user may further know the pill taking information through the external device. The wireless communication unit 84 may be one or more of a Bluetooth communication module, a WIFI communication module, and a mobile communication module (such as 2G, 3G, 4G, or 5G). For example, after the alarm 20 works, if the microprocessor 82 receives the rotation information of the pill box main body 10 transmitted by the vibration sensor 30, the microprocessor 82 may deduce that the user has taken out the pills through the pill box main body 10 and taken the pills. In a pill taking process, the pill box main body 10 is rotated, so that the microprocessor 82 may send the pill taking information to the mobile phone of the user or the mobile phone of other users (such as family members) through the wireless communication unit 84. The microprocessor 82 may further send at least one of alarm information, the system time, the pill taking reminding time, current pill grids information (or the number of the times of taking the pills) to the external device through the wireless communication unit 84.

Optionally, the microprocessor may further be connected to the vibration sensor and the alarm. After the alarm sends out remindings (for example, the reminding tone or a reminding light is sent out), if the vibration sensor detects the rotation information when the pill box rotates, the microprocessor may receive the rotation information detected by the vibration sensor, and the microprocessor controls the alarm to be turned off according to the rotation information. When the timer is reached for a preset time (such as a preset pill taking time), the timer sends corresponding information to the microprocessor, the microprocessor controls the alarm to send the prompt information according to the information, and the microprocessor simultaneously detects whether the vibration sensor has detected the rotation information of the pill box main body. It should be noted that, in some other embodiments, after the vibration sensor detects that the pill box main body rotates, a level of an output end of the vibration sensor may be changed (for example, a high level becomes a low level), and the level of the output end may turn off the alarm. The output end controls on and off of a power supply pin and a power supply end of the alarm through a switch tube (such as a field effect transistor). When the level of the output end changes, the power supply pin and the power supply end of the alarm are disconnected, so as to turn off the alarm. Compared with a control through the microprocessor, reaction of a level control of the output end of the vibration sensor is more rapid.

It should be noted that the intelligent pill box 1 in the present embodiments includes a circuit board 80. At least one of the microprocessor 82, the wireless communication unit 84, the vibration sensor 30, the loudspeaker 24, and the timer 40 is disposed on the circuit board 80.

The intelligent pill box provided by the embodiments of the present disclosure includes the plurality of pill grids and has functions of being configured to separate and place the pills, being accurately rotated the pill tray to turn to a target pill grid, regularly reminding, automatically turning off a reminding through detecting rotation of the intelligent pill box, and timely feeding back a state of the intelligent pill box to the external device such as a handheld device end through the wireless communication unit, so that the users are timely and effectively reminded to take the pills.

In order to better understand the intelligent pill box 1 in the embodiments, an use of the intelligent pill box 1 is exemplarily described below. Referring to FIG. 1 to FIG. 12, when using the intelligent pill box 1, the system time and a plurality of pill taking reminding time are firstly set through the time setting function key 60 and the timer 40, and then the corresponding system time and the preset pill taking reminding time are displayed on the display 50. At this time, the infrared sensing device 136 is correspondingly opposite to one of the detection notches 1343 on the shifting rod 134, the infrared sensing device 136 is turned on, namely that, the infrared receiver 1364 receives the infrared light sent by the infrared emitter 1362, the driving mechanism 132 does not work, the shifting rod 134 and the pill tray 160 do not rotate, and the pill taking port 181 is correspondingly opposite to one of the pill grids 162.

When the pill taking reminding time is reached, the microprocessor 82 controls the driving mechanism 132 to start working. The shifting rod 134 synchronously rotates, and the shifting pieces 1342 cooperate with the shifting grooves 164 to enable the pill tray 160 to rotate. At this time, the annular skirt 1344 passes through the infrared sensing device 136, and the infrared sensing device 136 is disconnected, namely that, the infrared receiver 1364 cannot receive the infrared light sent by the infrared emitter 1362. At the same time, the loudspeaker 24 of the alarm 20 sends out an alarm sound, and the prompting lamp 22 such as an LED light bar flashes to remind.

The driving mechanism 132 continues to work until when the next one of the detection notches 1343 is correspondingly opposite to the infrared sensing device 136, the infrared sensing device 136 is turned on. Then, the microprocessor 82 controls the driving mechanism 132 to stop working, so that the shifting rod 134 stops rotating. The pill tray 160 rotates to the next target pill grid 162 to be correspondingly opposite to the pill taking port 181. At the same time, the wireless communication unit 84 such as the Bluetooth communication module is wirelessly reported to the intelligent handheld device, and current pill taking status is recorded to remind the user to take the pills.

Then the user slides the sliding cover 184 to expose the pill taking port 181, turns the box body 120 vertically, and pours out the pills from the pill taking port 181. The vibration sensor 30 is turned on, the loudspeaker 24 of the alarm 20 stops alarming, the prompting light 22 such as the LED light bar stops flashing, and finally the sliding cover 184 is slid to close the pill taking port 181, the box body 120 is laid flat to wait for next time to take the pills.

The intelligent pill box provided by the embodiments of the present disclosure is described in detail above. Principles and the embodiments of the present disclosure are set forth in the present document. Description of the above embodiments is merely configured to help to understand methods of the present disclosure and core idea of the present disclosure. Meanwhile, for the person skilled in the art, according to the idea of the present disclosure, there are changes in specific implementation modes and the application ranges. In summary, content of the present disclosure should not be construed as limiting the present disclosure.

What is claimed is:

1. An intelligent pill box, comprising:
   a pill box main body;
   an alarm;
   a vibration sensor;
   wherein the pill box main body is configured to store pills;
   the alarm is disposed in the pill box main body, and the alarm is configured to remind a user to take the pills;
   the vibration sensor is disposed in the pill box main body, and the vibration sensor is configured to turn off the alarm when the vibration sensor detects that the pill box main body is rotated;
   the pill box main body comprises a box body, a box cover assembly, a cover body, and a pill tray; the box cover assembly is connected with the box body, an accommodating space is formed between the box cover assembly and the box body, a pill taking port is defined on the box cover assembly; the cover body is disposed in the accommodating space; the pill tray is disposed in the accommodating space, a mounting hole is defined in a middle of the pill tray, and the pill tray is sleeved on the cover body through the mounting hole; the pill tray comprises a plurality of pill grids surrounding the cover body, and the pill tray rotates relative to the box cover assembly, so that one of the plurality of the pill grids is correspondingly opposite to the pill taking port;
   the pill box main body further comprises a driving mechanism and a shifting rod; the driving mechanism is disposed in the accommodating space; a first end of the shifting rod is connected with the driving mechanism, a second end of the shifting rod is in driving connection with the pill tray; and the driving mechanism drives the shifting rod to rotate, so that the shifting rod drives the pill tray to rotate;
   a plurality of shifting grooves are defined in one side, distal from the box cover assembly, of the pill tray; shifting pieces are disposed on the second end of the shifting rod, and the shifting pieces are clamped into the shifting grooves to drive the pill tray to rotate;
   the driving mechanism comprises a motor, a reduction gear set, and an output gear; the motor is disposed on the box body; the reduction gear set is connected to an output end of the motor; the output gear is rotatably connected with the reduction gear set, and the output gear is further detachably connected with the shifting rod;
   the shifting rod comprises an annular skirt having a plurality of notches;
   the intelligent pill box further comprises an infrared sensing device, the infrared sensing device comprises an infrared emitter and an infrared receiver, the infrared emitter and the infrared receiver are disposed on two sides of the annular skirt;
   when the annular skirt is rotated between the infrared emitter and the infrared receiver, the infrared receiver cannot receive infrared light emitted by the infrared emitter, and the infrared receiver controls the alarm to emit reminding information; and
   when the notches are located between the infrared emitter and the infrared receiver, the infrared receiver receives the infrared light emitted by the infrared emitter, and the infrared receiver controls the driving mechanism to stop working.

2. The intelligent pill box according to claim 1, wherein the intelligent pill box further comprises a timer; the timer is disposed on the pill box main body, and the timer is configured to control the driving mechanism to start working when preset time of the timer is arrived, so that the annular skirt is rotated between the infrared emitter and the infrared receiver.

3. The intelligent pill box according to claim 1, wherein the box cover assembly comprises a box cover and a sliding cover; the sliding cover is slidably disposed on the box cover, and the sliding cover slides relative to the box cover so as to block the pill taking port or expose the pill taking port.

4. The intelligent pill box according to claim 1, wherein the box cover assembly further comprises an observation port, the observation port is adjacent to the pill taking port where the pill taking port is correspondingly opposite to the one of the plurality of the pill grids, each of the pill grids of the pill tray is provided with a corresponding number of times of taking pills and the observation port is configured to show the corresponding number of the times of taking the pills of each of the pill grids.

5. The intelligent pill box according to claim 1, wherein the intelligent pill box further comprises:
   a display; and
   a time setting function key;
   the display is disposed on the pill box main body, the display is configured to display a system time and set a pill taking reminding time; the time setting function key is disposed on the pill box main body, and the time setting function key is configured to adjust the system time and preset the pill taking reminding time.

6. The intelligent pill box according to claim 5, wherein the display is disposed on the box body, a first through hole, corresponding to the display, is defined on the cover body; and a material of the box cover assembly is a transparent material.

7. The intelligent pill box according to claim 1, wherein the box body further comprises a lock pin groove, a lock hole, corresponding to the lock pin groove, is defined on the box cover assembly; the intelligent pill box further comprises a lock pin, and the lock pin penetrates through the lock pin groove to lock with the lock hole, so as to tightly lock the box body and the box cover assembly.

8. The intelligent pill box according to claim 7, wherein the lock pin rotates relative to the lock hole to lock or unlock the lock pin with the lock hole.

9. The intelligent pill box according to claim 8, wherein the intelligent pill box further comprises a key, the key is detachably connected with the lock pin, and the key drives the lock pin to rotate.

10. The intelligent pill box according to claim 9, wherein a key groove is defined in one side, distal from the box cover assembly, of the box body; and the key is detachably disposed in the key groove.

11. The intelligent pill box according to claim 1, wherein the alarm comprises a prompting lamp, and the prompting lamp is disposed on one side, facing the box cover assembly, of the cover body.

12. The intelligent pill box according to claim 1, wherein the alarm comprises a loudspeaker, and the loudspeaker is disposed in the pill box main body.

13. The intelligent pill box according to claim 1, wherein the intelligent pill box further comprises a microprocessor and a wireless communication unit, both the vibration sensor and the wireless communication unit are connected with the microprocessor, the microprocessor acquires rotation information, detected by the vibration sensor, of the pill box main body, and the microprocessor sends the rotation information to external equipment through the wireless communication unit.

* * * * *